(12) United States Patent
Yamauchi

(10) Patent No.: US 7,399,925 B2
(45) Date of Patent: Jul. 15, 2008

(54) STRUCTURE OF GAS SENSOR ENSURING STABILITY OF ELECTRICAL CONNECTION

(75) Inventor: Masanobu Yamauchi, Kariya (JP)

(73) Assignee: Denso Corporation, Kariya, Aichi-Pref. (JP)

( * ) Notice: Subject to any disclaimer, the term of this patent is extended or adjusted under 35 U.S.C. 154(b) by 0 days.

(21) Appl. No.: 11/798,992

(22) Filed: May 18, 2007

(65) Prior Publication Data

US 2007/0272431 A1   Nov. 29, 2007

(30) Foreign Application Priority Data

May 26, 2006   (JP)   ............................. 2006/146670

(51) Int. Cl.
*H02G 15/02*   (2006.01)
(52) U.S. Cl. .................. 174/74 R; 174/77 R; 204/424; 439/33
(58) Field of Classification Search ............... 174/74 R, 174/97, 77 R, 84 R, 91, 135, 138, 137 R; 204/424; 73/31.05; 439/33, 886, 874, 891
See application file for complete search history.

(56) References Cited

U.S. PATENT DOCUMENTS

| | | | | |
|---|---|---|---|---|
| 5,949,023 A | * | 9/1999 | Weyl | .......................... 174/77 R |
| 6,150,607 A | * | 11/2000 | Weyl et al. | ................... 174/667 |
| 6,231,348 B1 | * | 5/2001 | Mayer et al. | ................... 439/33 |
| 6,246,000 B1 | * | 6/2001 | Wehrmann et al. | ........ 174/74 R |

FOREIGN PATENT DOCUMENTS

JP        2004-144732        5/2004

* cited by examiner

*Primary Examiner*—Dhiru R Patel
(74) *Attorney, Agent, or Firm*—Nixon & Vanderhye PC

(57) ABSTRACT

A gas sensor includes a sensor element, a housing, a hollow porcelain insulator, electrical contacts, a holder, and an air cover. The sensor element is retained inside the housing through the porcelain insulator. The electrical contacts are retained firmly within the porcelain insulator in electrical connection with the sensor element. The air cover is joined to the housing to cover the porcelain insulator. The holder is fit on the porcelain insulator and has stopper springs which are in elastic abutment with an inner shoulder surface of the air cover, thereby stopping the porcelain insulator from moving vertically when the contacts are pulled undesirably through lead wires in order to ensure the stability of electrical connection with the sensor element.

12 Claims, 6 Drawing Sheets

STRUCTURE OF GAS SENSOR ENSURING STABILITY OF ELECTRICAL CONNECTION

CROSS REFERENCE TO RELATED DOCUMENT

The present application claims the benefit of Japanese Patent Application No. 2006-146670 filed on May 26, 2006, the disclosure of which is totally incorporated herein by reference.

BACKGROUND OF THE INVENTION

1. Technical Field of the Invention

The present invention relates generally to a gas sensor which is installed, for example, in an exhaust system of automotive internal combustion engines to measure a preselected component of exhaust emissions, and more particularly to an improved structure of such a gas sensor which is designed to ensure the stability of electrical connection between contacts and mating parts in the gas sensor.

2. Background Art

There are known gas sensors installed in an exhaust system of automotive internal combustion engines. Japanese Patent First Publication No. 2004-144732 teaches such a type of a gas sensor 9, as illustrated in FIG. 7, designed to measure the concentration of oxygen or nitrogen oxides (NOx) contained in exhaust emissions from the engine.

The gas sensor 9 includes a plate-shaped sensor element 92 responsive to gas to be measured and a porcelain insulator 93 within which the sensor element 92 is retained. The porcelain insulator 93 is fit in a housing 94. A porcelain insulator 95 is disposed above the porcelain insulator 93 to cover a base end 921 (i.e., an upper end, as viewed in the drawing) of the sensor element 92. An air cover 95 is joined to a base end (i.e., an upper end, as viewed in the drawing) of the housing 94 to cover the porcelain insulator 95.

Within the porcelain insulator 95, contacts 97 are disposed in electrical contact with terminals affixed to the sensor element 92. The contacts 97 are joined to leads 98.

The structure of the gas sensor 9, however, has the following drawback.

When the leads 98 are pulled undesirably from outside the gas sensor 9, it will cause the contacts 97 to be also pulled to the base end of the gas sensor 9. In the worst case, the contacts 97 are dislodged out of the porcelain insulator 95, so that they are electrically disconnected from the sensor element 92. Even if the contacts 97 are held firmly within the porcelain insulator 95, they may slide vertically along with the porcelain insulator 95, which results in electrical disconnection of the contacts 97 from the sensor element 92.

SUMMARY OF THE INVENTION

It is therefore a principal object of the invention to avoid the disadvantages of the prior art.

It is another object of the invention to provide an improved structure of a gas sensor which is designed to ensure the stability of electrical connection between contacts and mating parts disposed in the gas sensor.

According to one aspect of the invention, there is provided an improved structure of a gas sensor which may be employed in measuring the concentration of a given component of exhaust emissions from automotive engines. The gas sensor has a length with a top end and a base end opposite the top end and comprises: (a) a sensor element having a length with a top end and a base end opposite the top end, the sensor element being responsive to a gas to output a signal as a function of a concentration of the gas; (b) a housing having a top end and a base end opposite the top end, the housing retaining the sensor element therewithin; (c) a hollow porcelain insulator having a top end and a base end opposite the top end, the porcelain insulator being disposed on a side of the base end of the housing to cover the base end of the sensor element, the porcelain insulator having a protrusion formed on the top end thereof and a stopper formed therein; (d) a contact member disposed inside the porcelain insulator in electrical contact with a terminal of the sensor element, the contact member having a stopper which is placed in engagement with the stopper of the porcelain insulator for stopping the contact member from moving outside the porcelain insulator; (e) a holder having a top end and a base end opposite the top end, the holder grasping an outer surface of the porcelain insulator in engagement of the top end thereof with the protrusion of the porcelain insulator; (f) a cover disposed on the side of the base end of the housing in connection with the housing to cover the porcelain insulator, the cover having an inner stopper formed on an inner wall thereof; and (g) a holder stopper formed on the holder which is designed to abut the inner stopper of the cover to stop the holder from moving to the base end of the gas sensor to hold the porcelain insulator from moving to the base end of the gas sensor through the engagement of the top end of the holder with the protrusion of the porcelain insulator.

If the contact member is undesirably pulled through, for example, a lead wire, the engagement of the stopper of the contact member with the stopper of the porcelain insulator works to hold the contact member from moving outside the porcelain insulator.

When such force to pull the contact member acts on the porcelain insulator, it will cause the engagement of the protrusion of the porcelain insulator with the top end of the holder to operate to urge the holder stopper against the inner stopper of the cover to stop the holder from moving undesirably relative to the cover.

The cover is connected to the housing. The sensor element is retained by the housing. Therefore, unless moved relative to the cover, the porcelain insulator is not moved out of alignment with the sensor element. The contact member is also held in place within the porcelain insulator, thus ensuring the stability of electrical contact with the sensor element.

In the preferred mode of the invention, the holder stopper is designed to be elastically deformable when subjected to pressure oriented in a lengthwise direction of the gas sensor, thereby absorbing a variation in dimension of the holder. This also facilitates the ease of installation of the holder in abutment of the holder stopper with the inner stopper of the cover.

The holder stopper has a bend which permits the holder stopper to be elastically deformed when subjected to the pressure.

The holder grasps 50% or more of a circumference of the outer surface of the porcelain insulator, thereby ensuring the stability in retaining the porcelain insulator.

According to the second aspect of the invention, there is provided a gas sensor having a length with a top end and a base end opposite the top end which comprises: (a) a sensor element having a length with a top end and a base end opposite the top end, the sensor element being responsive to a gas to output a signal as a function of a concentration of the gas; (b) a housing having a top end and a base end opposite the top end, the housing retaining the sensor element therewithin; (c) a hollow porcelain insulator having a top end and a base end opposite the top end, the porcelain insulator being disposed on a side of the base end of the housing to cover the base end of the sensor element, the porcelain insulator having a protrusion formed on the top end thereof and a stopper formed therein; (d) a contact member disposed inside the porcelain insulator in electrical contact with a terminal of the sensor element, the contact member having a stopper which is placed in engagement with the stopper of the porcelain insulator for stopping the contact member from moving outside the porcelain insulator; (e) a holder having a top end and a base end opposite the top end, the holder grasping an outer surface of the porcelain insulator in engagement of the top end thereof with the protrusion of the porcelain insulator; (f) a cover disposed on the side of the base end of the housing in connection with the housing to cover the porcelain insulator; (g) a protective cylinder having a top end and a base end opposite the top end, the protective cylinder being joined to the housing and located outside the porcelain insulator within the cover; (h) a holder stopper formed on the holder, the holder stopper being urged into abutment with an inner surface of the protective cylinder; and (i) a protrusion formed on the base end of the protective cylinder. The protrusion extends inwardly of the protective cylinder to server as a stopper which is designed to abut the holder stopper to stop the holder from moving to the base end of the gas sensor to hold the porcelain insulator from moving to the base end of the gas sensor through the engagement of the top end of the holder with the protrusion of the porcelain insulator.

If the contact member is undesirably pulled through, for example, a lead wire, the engagement of the stopper of the contact member with the stopper of the porcelain insulator works to hold the contact member from moving outside the porcelain insulator.

When such force to pull the contact member acts on the porcelain insulator, it will cause the engagement of the protrusion of the porcelain insulator with the top end of the holder to operate to urge the holder stopper against the protrusion of the protective cylinder to hold the porcelain insulator from moving undesirably relative to the protective cylinder.

The protective cylinder is joined to the housing. The sensor element is also retained by the housing. Therefore, unless moved relative to the protective cylinder, the porcelain insulator is not moved out of alignment with the sensor element. The contact member is also held in place within the porcelain insulator, thus ensuring the stability of electrical contact with the sensor element.

When the cover is subjected to an external force and deformed, the space between the cover and the protective cylinder serves to absorb such deformation, thereby avoiding the breakage of the sensor element.

In the preferred mode of the invention, the holder grasps 50% or more of a circumference of the outer surface of the porcelain insulator.

According to the third aspect of the invention, there is provided a gas sensor having a length with a top end and a base end opposite the top end which comprises: (a) a hollow cylindrical sensor element with a bottom which has a length with a top end and a base end opposite the top end, the sensor element being responsive to a gas to output a signal as a function of a concentration of the gas; (b) a housing having a top end and a base end opposite the top end, the housing retaining the sensor element therewithin; (c) a heater having a top end and a base end opposite the top end, the heater being disposed inside the sensor element with the base end thereof protruding outside the sensor element to heat the sensor element; (d) a hollow porcelain insulator having a top end and a base end opposite the top end, the porcelain insulator being disposed on a side of the base end of the housing to cover the base end of the heater, the porcelain insulator having a protrusion formed on the top end thereof and a stopper formed therein; (e) a contact member disposed inside the porcelain insulator in electrical contact with a terminal of the heater, the contact member having a stopper which is placed in engagement with the stopper of the porcelain insulator for stopping the contact member from moving outside the porcelain insulator; (f) a holder having a top end and a base end opposite the top end, the holder grasping an outer surface of the porcelain insulator in engagement of the top end thereof with the protrusion of the porcelain insulator; (g) a cover disposed on the side of the base end of the housing in connection with the housing to cover the porcelain insulator, the cover having an inner stopper formed on an inner wall thereof; and (h) a holder stopper formed on the holder which is designed to abut the inner stopper of the cover to stop the holder from moving to the base end of the gas sensor to hold the porcelain insulator from moving to the base end of the gas sensor through the engagement of the top end of the holder with the protrusion of the porcelain insulator.

If the contact member is undesirably pulled through, for example, a lead wire, the engagement of the stopper of the contact member with the stopper of the porcelain insulator works to hold the contact member from moving outside the porcelain insulator.

When such force to pull the contact member acts on the porcelain insulator, it will cause the engagement of the protrusion of the porcelain insulator with the top end of the holder to operate to urge the holder stopper against the inner stopper of the cover to stop the holder from moving undesirably relative to the cover.

The cover is connected to the housing. The heater is disposed inside the housing through the sensor element. Therefore, unless moved relative to the cover, the porcelain insulator is not moved out of alignment with the heater. The contact member is also held in place within the porcelain insulator, thus ensuring the stability of electrical contact with the sensor element.

In the preferred mode of the invention, the holder stopper is designed to be elastically deformable when subjected to pressure oriented in a lengthwise direction of the gas sensor.

The holder stopper has a bend which permits the holder stopper to be elastically deformed when subjected to the pressure.

The holder grasps 50% or more of a circumference of the outer surface of the porcelain insulator.

According to the fourth aspect of the invention, there is provided a gas sensor having a length with a top end and a base end opposite the top end which comprises: (a) a hollow cylindrical sensor element with a bottom which has a length with a top end and a base end opposite the top end, the sensor element being responsive to a gas to output a signal as a function of a concentration of the gas; (b) a housing having a top end and a base end opposite the top end, the housing retaining the sensor element therewithin; (c) a heater having a top end and a base end opposite the top end, the heater being disposed inside the sensor element with the base end thereof protruding outside the sensor element to heat the sensor element; (d) a hollow porcelain insulator having a top end and a base end opposite the top end, the porcelain insulator being disposed on a side of the base end of the housing to cover the base end of the heater, the porcelain insulator having a protrusion formed on the top end thereof and a stopper formed therein; (e) a contact member disposed inside the porcelain insulator in electrical contact with a terminal of the heater, the contact member having a stopper which is placed in engagement with the stopper of the porcelain insulator for stopping the contact member from moving outside the porcelain insulator; (f) a holder having a top end and a base end opposite the top end, the holder grasping an outer surface of the porcelain insulator in engagement of the top end thereof with the protrusion of the porcelain insulator; (g) a cover disposed on the side of the base end of the housing in connection with the housing to cover the porcelain insulator, the cover having an inner stopper formed on an inner wall thereof; (h) a protective cylinder having a top end and a base end opposite the top end, the protective cylinder being joined to the housing and located outside the porcelain insulator within the cover; (i) a holder stopper formed on the holder, the holder stopper being urged into abutment with an inner surface of the protective cylinder; and (j) a protrusion formed on the base end of the protective cylinder. The protrusion extends inwardly of the protective cylinder to server as a stopper which is designed to abut the holder stopper to stop the holder from moving to the base end of the gas sensor to hold the porcelain insulator from moving to the base end of the gas sensor through the engagement of the top end of the holder with the protrusion of the porcelain insulator.

If the contact member is undesirably pulled through, for example, a lead wire, the engagement of the stopper of the contact member with the stopper of the porcelain insulator works to hold the contact member from moving outside the porcelain insulator.

When such force to pull the contact member acts on the porcelain insulator, it will cause the engagement of the protrusion of the porcelain insulator with the top end of the holder to operate to urge the holder stopper against the protrusion of the protective cylinder to hold the porcelain insulator from moving undesirably relative to the protective cylinder.

The protective cylinder is joined to the housing. The heater is disposed inside the housing through the sensor element. Therefore, unless moved relative to the protective cylinder, the porcelain insulator is not moved out of alignment with the heater. The contact member is also held in place within the porcelain insulator, thus ensuring the stability of electrical contact with the heater.

When the cover is subjected to an external force and deformed, the space between the cover and the protective cylinder serves to absorb such deformation, thereby avoiding the breakage of the sensor element.

In the preferred mode of the invention, the holder grasps 50% or more of a circumference of the outer surface of the porcelain insulator.

BRIEF DESCRIPTION OF THE DRAWINGS

The present invention will be understood more fully from the detailed description given hereinbelow and from the accompanying drawings of the preferred embodiments of the invention, which, however, should not be taken to limit the invention to the specific embodiments but are for the purpose of explanation and understanding only.

In the drawings.

DESCRIPTION OF THE PREFERRED EMBODIMENTS

Figure 1:
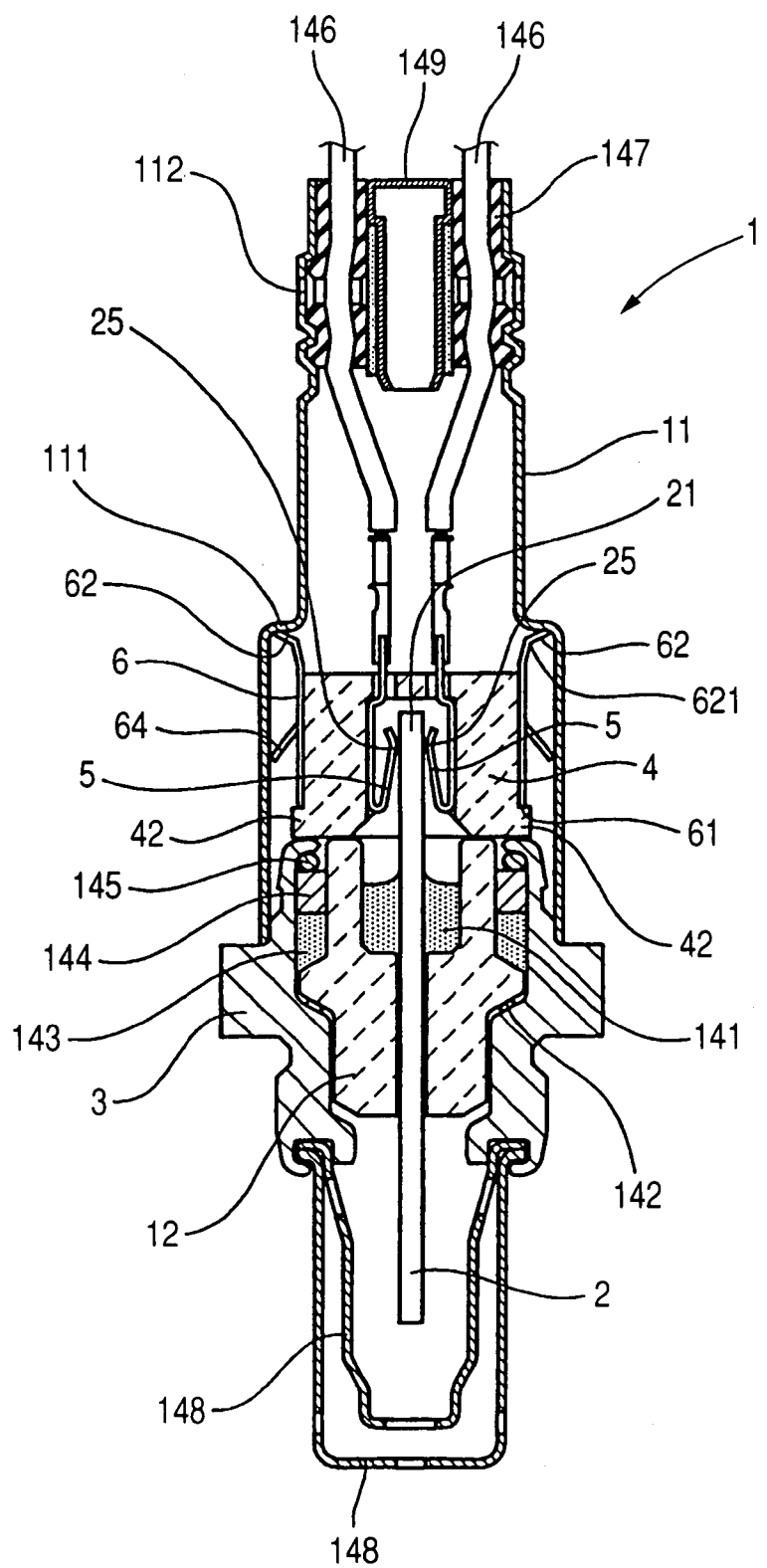
FIG. 1 is a longitudinal sectional view which shows a structure of a gas sensor according to the first embodiment of the invention.

Referring to the drawings, wherein like reference numbers refer to like parts in several views, particularly to FIGS. 1 to 4, there is shown a gas sensor 1 according to the first embodiment of the invention which is designed to be installed in an exhaust pipe of an automotive internal combustion engine to measure the concentration of a component such as $O_2$, NOx, CO, or HC contained in exhaust gas for burning control of the engine. The gas sensor 1 may be implemented as an air-fuel ratio sensor (also called A/F sensor) for use in an exhaust gas feedback system. The gas sensor 1 may also be implemented as a NOx sensor for use in monitoring the deterioration of a three-way catalyst.

The gas sensor 1 includes a sensor element 2, a housing 3, an atmosphere-side porcelain insulator 4, and an air cover 11. The sensor element 2 is designed to be responsive to the preselected component of exhaust gas to produce an electrical signal as a function of the concentration thereof. The sensor element 2 is retained in the housing 3. The porcelain insulator 4 is placed on a base end (i.e., an upper end, as viewed in FIG. 1) of the housing 3 to surround a base end portion 21 of the sensor element 2. The porcelain insulator 4 has retained therein spring contacts 5 which makes electrical connections with terminals 25 affixed to the sensor element 2. The porcelain insulator 4 is retained firmly within the air cover 11 by a hollow cylindrical holder 6, as clearly illustrated in FIGS. 3 and 4. The air cover 11 is joined to the base end of the housing 3.

Figure 2:
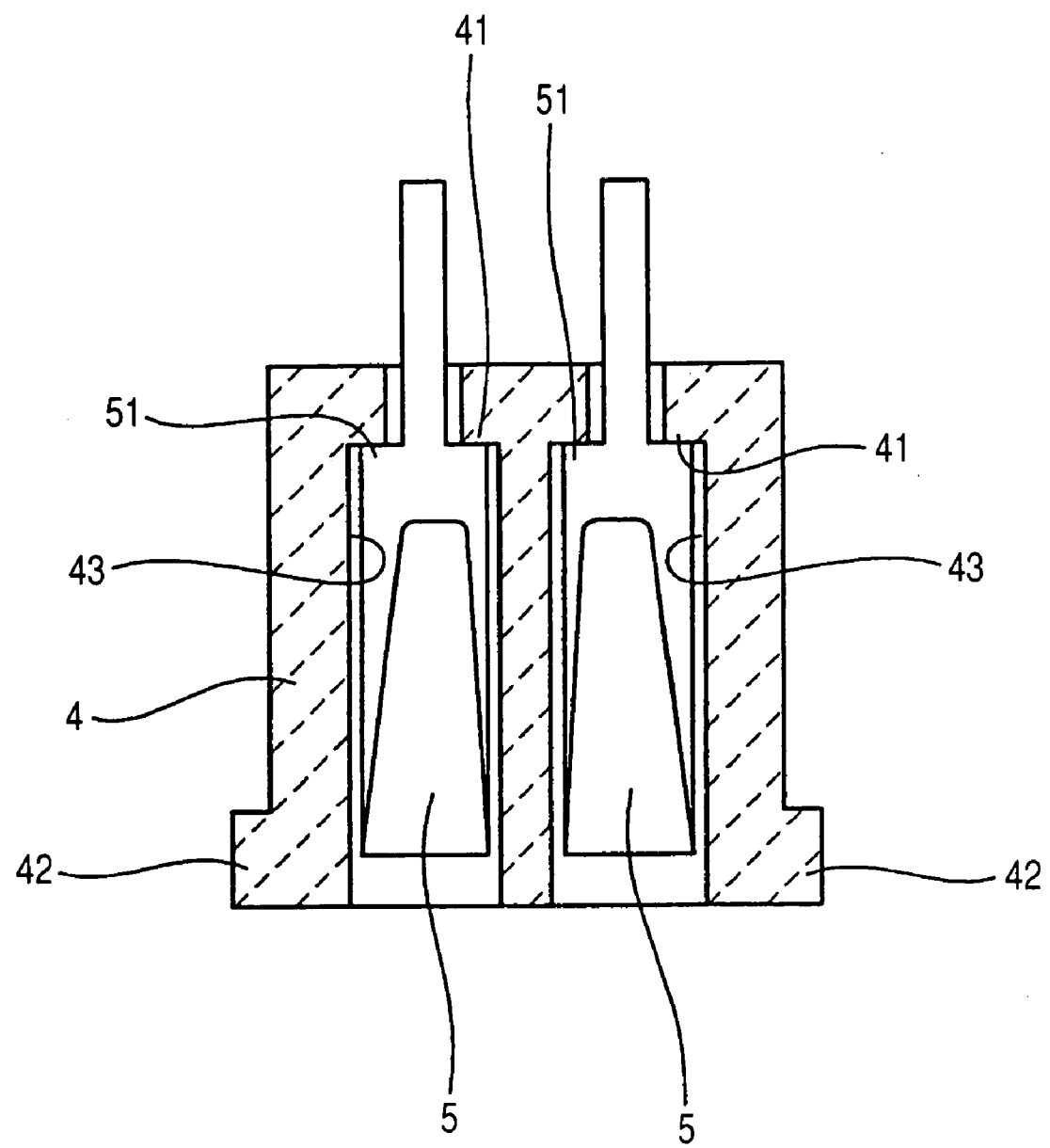
FIG. 2 is a partially enlarged view which shows a porcelain insulator disposed inside the gas sensor of FIG. 1.

The porcelain insulator 4, as clearly illustrated in FIG. 2, has formed in an inner wall thereof four rectangular contact chambers 43 within which the spring contacts 5 are disposed, respectively. Each of the contact chambers 43 has a pair of inner shoulders 41 functioning as stoppers. Similarly, each of the spring contacts 5 has a pair of shoulders 51 serving as stoppers which are placed in abutment with the inner shoulders 41 of a corresponding one of the contact chambers 43 to stop or hold the spring contact 5 from being dislodged out of the porcelain insulator 4. The porcelain insulator 4 also has a top flange 42 extending around the whole of a circumference of a top end (i.e., a lower end, as viewed in FIG. 2) thereof. In place of the top flange 42, one or a plurality of protrusions or tabs may be formed on the circumference of the porcelain insulator 4. The tabs may preferably be diametrically opposed to each other, that is, located symmetrically with respect to the center of the porcelain insulator 4.

The holder 6 has two stopper spring strips 62 extending outwardly. The stopper spring strips 62 are placed in abutment with an inner surface of an annular shoulder 111 of the air cover 11 and serve as retainers and stoppers to position the holder 6 in the air cover 11 in an axial direction of the air cover 11. Each of the stopper spring strips 62, as clearly illustrated in FIG. 4, has a bend 621 to permit the stopper spring strip 62 to be deformed elastically as a mechanical spring in an axial direction of the holder 6. The stopper spring strips 62 may alternatively be located at a given gap away from the inner surface of the shoulder 111. In this case, it is advisable that the gap or distance between each of the stopper spring strips 62 and the inner surface of the shoulder 111 be selected within a range which keeps the spring contacts 5 in electric contact with the sensor element 2 when the holder 6 moves relative to the air cover 11.

Figure 3:
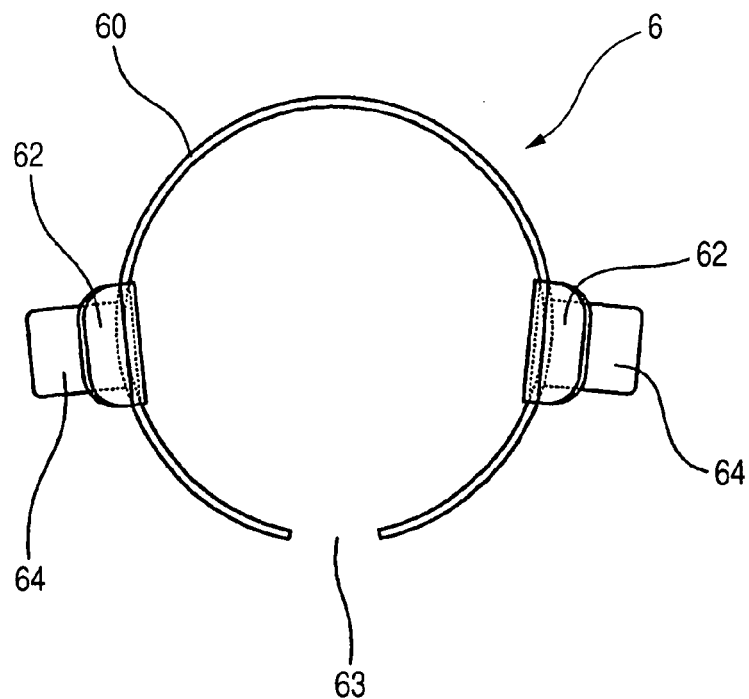
FIG. 3 is a top view which shows a holder for retaining the porcelain insulator of FIG. 2.

The holder 6 is designed to occupy or grasp 50% or more of a circumferential outer surface of the porcelain insulator 4. In this embodiment, the holder 6 is, as illustrated in FIG. 3, made of a hollow cylindrical body 60 with a slit 63 to have a C-shape in cross section. The body 60 is fit over 50% (i.e., 180°) or more of the circumference of the porcelain insulator 4.

Figure 4:
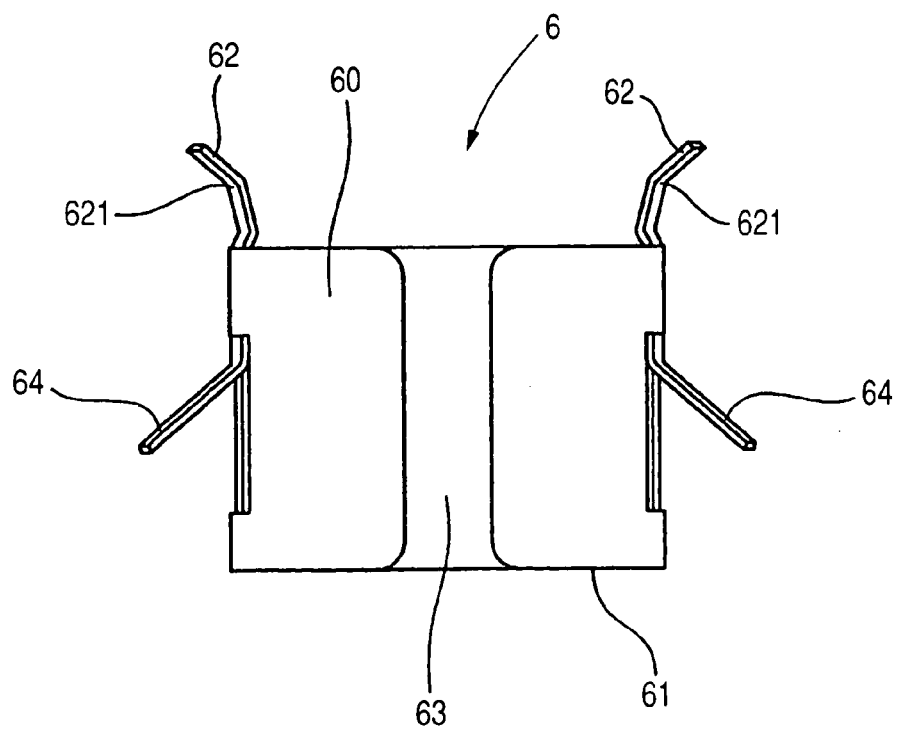
FIG. 4 is a side view of FIG. 3.

The two stopper spring strips 62, as clearly illustrated in FIGS. 3 and 4, extend from a base edge (i.e., an upper edge, as viewed in FIG. 1) of the body 60 of the holder 6 and are bent outwardly. The holder 6 may alternatively have three or more stopper spring strips.

The body 60 of the holder 6 also has two retainer spring strips 64 which extend outward from the peripheral wall thereof. The retainer spring strips 64 are urged into elastical abutment with an inner wall of the air cover 11 to retain the holder 6 within the air cover 11. The retainer spring strips 64 are designed to be elastically deformable in a radius direction of the holder 6 when the body 60 of the holder 6 undergoes a lateral pressure. In other words, the retainer spring strips 64 serve to permit the body 60 of the holder 6 to move or vibrate in the same direction as that in which the spring contacts 5 are deformable. When the gas sensor 1 is subjected to an external impact force, the retainer spring strips 64 work to absorb such a force to protect the sensor element 2.

The sensor element 2 is of a typical structure formed by a lamination of ceramic layers made of alumina ($Al_2O_3$) and zirconia ($ZrO_2$). The sensor element 2 is equipped with a sensor cell and a heater (not shown). The sensor cell is responsive to, for example, oxygen or nitrogen oxide (NOx) contained in exhaust emissions from automotive internal combustion engines to produce a signal as a function of the concentration thereof. The heater works to heat the sensor cell up to a desired activation temperature.

The sensor element 2 is, as illustrated in FIG. 1, fit in a sensor element-side porcelain insulator 12. The clearance between the sensor element 2 and the porcelain insulator 12 is hermetically sealed by a glass seal 141. The glass seal 141 also serves to retain the sensor element 2 firmly in the porcelain insulator 12. The porcelain insulator 12 is fit in the housing 3. A gasket ring 142 is disposed between the housing 3 and the porcelain insulator 12. Between the porcelain insulator 12 and the housing 3, an annular sealing member 143, an insulating member 144, and a metal ring 145 are laid to overlap each other and compressed by crimping the base end of the housing 3 inwardly to hold the porcelain insulator 12 firmly within the housing 3.

The atmosphere-side porcelain insulator 4 and the sensor element-side porcelain insulator 12 are each made of ceramic such as alumina ($Al_2O_3$) or steatite ($MgO.SiO_2$).

The four spring contacts 5 are, as described above, disposed inside the porcelain insulator 4. Two of the spring contacts 5 are placed in electrical contact with output terminals of the sensor cell of the sensor element 2, while the other two of the spring contacts 5 are placed in electrical contact with power supply terminal of the heater affixed to the sensor cell. Each of the spring contacts 5 is made of a metal strip bent into a substantially C-shape.

Each of the spring contacts 5, as described above, has the shoulders 51 extending perpendicular to the length thereof. The porcelain insulator 4 has formed in the inner wall thereof the four rectangular contact chambers 43 within which the spring contacts 5 are disposed, respectively. Each of the contact chambers 43 has the inner shoulders 41 with which the shoulders 51 of one of the spring contacts 5 are placed in abutment.

Each of the spring contacts 5 is, as illustrated in FIG. 1, joined electrically to one of leads 146. The leads 146 extend through a rubber bush 147 outside the gas sensor 1. The rubber bush 147 is fit hermetically in an open end of the air cover 11.

A cylindrical member 149 with a closed base end is disposed within the rubber bush 147. The cylindrical member 149 is designed to establish fluid communication between air inlets 112 formed in the air cover 11 and inside the air cover 11 to introduce air having entered the air inlets 112 into the air cover 11 through the cylindrical member 149.

The air cover 11 is welded at a top end (i.e., a lower end, as viewed in FIG. 1) thereof to the housing 3 or may alternatively be crimped to make a joint to the housing 3. The air cover 11 includes a large-diameter portion within which the porcelain insulator 4 is disposed and a small-diameter portion which extends from the large-diameter portion to the base end of the air cover 11 and defines between itself and the large-diameter portion the shoulder 111 with which the stopper spring strips 62 is placed in elastic abutment.

The gas sensor 1 also includes a protective cover assembly 148 which is joined to the top end of the housing 3 to cover a sensing portion of the sensor element 2 which is to be exposed to gas having entered inside the protective cover assembly 148.

The beneficial features of the structure of the gas sensor 1 will be described below.

Each of the spring contacts 5 has the shoulders 51 serving as stoppers which are placed in abutment with the inner shoulders 41 of a corresponding one of the contact chambers 43 to stop the spring contact 5 from being dislodged out of the porcelain insulator 4 when the lead 146 is pulled undesirably outside the gas sensor 1.

When any of the leads 146 is pulled outward, the porcelain insulator 4 is also pulled by the spring contact 5 to the base end of the gas sensor 1. The top flange 61 of the porcelain insulator 4 is in engagement with the top end 61 of the holder 6, thus causing the stopper spring strips 62 to absorb the pulling of the porcelain insulator 4 to hold the porcelain insulator 4 in place within the air cover 11.

The air cover 1 is joined to the housing 3. The sensor element 2 is also retained by the housing 3. Therefore, unless moved relative to the air cover 11, the porcelain insulator 4 is not moved out of alignment with the sensor element 2. The spring contacts 5 are also held in place within the porcelain insulator 4, thus ensuring the stability of electrical contact with the sensor element 2.

Specifically, the structure of the gas sensor 1 is designed to hold the spring contacts 5 in place within the porcelain insulator 4 free from the action of external force pulling the spring contacts 5 outside the porcelain insulator 4, thus ensuring the stability of electrical contact with the terminals 25 of the sensor element 2.

The bend 621 of each of the stopper spring strips 62 permits elastic deformation of the stopper spring strip 62 to absorb a variation in dimension of the holder 6, thus facilitating ease of installation of the holder 6 in the porcelain insulator 4.

The holder 6 is, as described above, designed to occupy 50% or more of the circumferential outer surface of the porcelain insulator 4, thereby ensuring the stability in retaining the porcelain insulator 4 and minimizing a physical shift of the porcelain insulator 4 from the holder 6 to assure the electrical contact of the spring contacts 5 with the sensor element 2 when the external force acts on the porcelain insulator 4 to pull it through the spring contacts 5.

Figure 5:
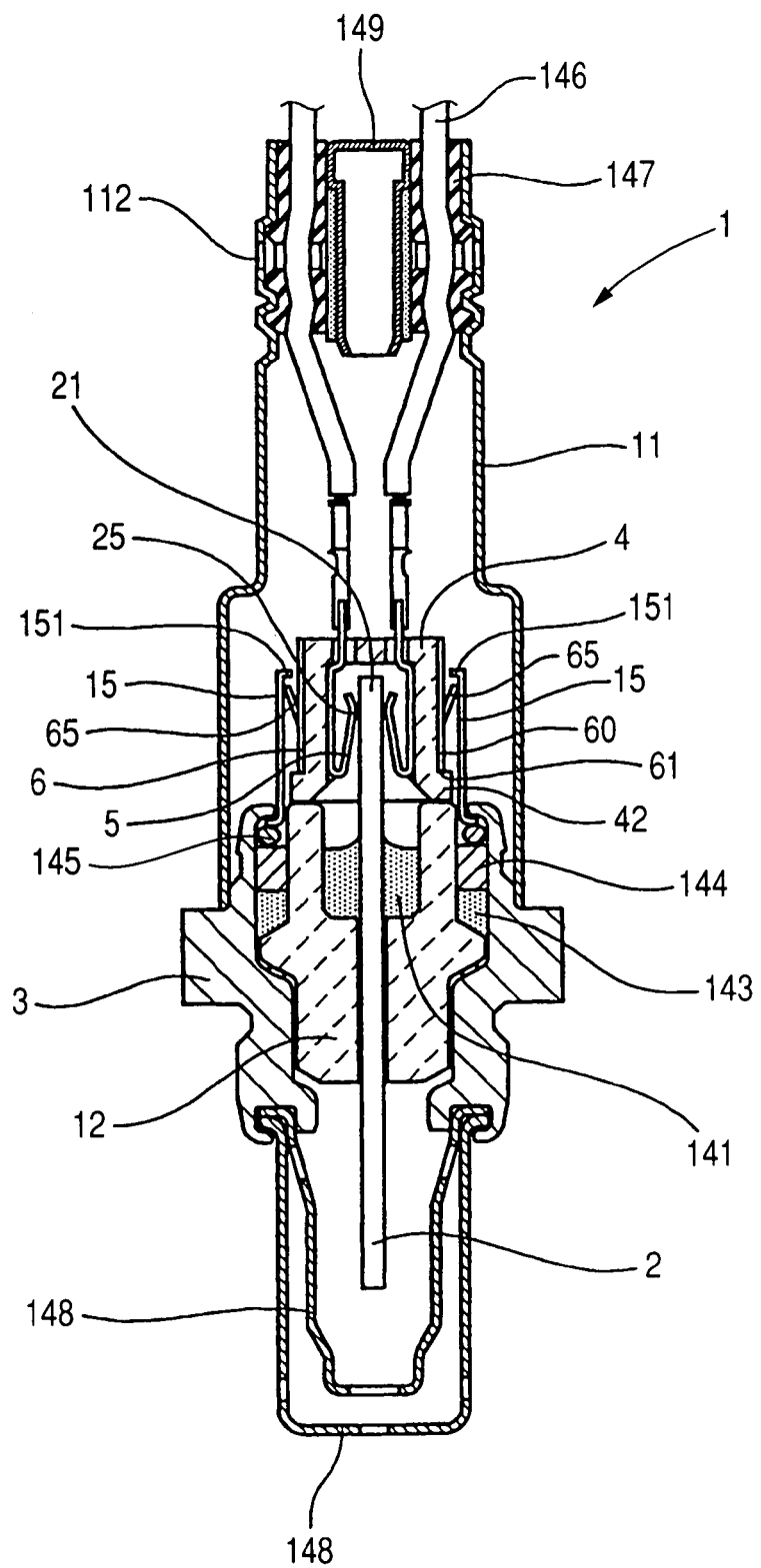
FIG. 5 is a longitudinal sectional view which shows a structure of a gas sensor according to the second embodiment of the invention.

FIG. 5 illustrates the gas sensor 1 according to the second embodiment of the invention in which a hollow protective cylinder 15 is joined to the housing 3 to retain therein the porcelain insulator 4 through the holder 6.

The holder 6 has two or more retainer/stopper spring strips 65 which have substantially the same structure as those in the retainer spring strips 64 and extend upward, as viewed in FIG. 5. The retainer/stopper spring strips 65 are placed in elastic abutment with an inner wall of the protective cylinder 15. The protective cylinder 15 has an inner flange 151 extending inwardly from a base end (i.e., an upper end, as viewed in the drawing) thereof. The inner flange 151 works as a stopper to stop the retainer/stopper spring strips 65 from sliding out of the protective cylinder 15.

The joint of the protective cylinder 15 to the housing 3 is achieved by crimping the base end of the housing 3 inwardly to nip a top end of the protective cylinder 15 between the base end of the housing 3 and the metal ring 145.

The retainer/stopper spring strips 65 extend from the outer side wall of the body 60 of the holder 6 upward and outward, as viewed in the drawing.

Each of the retainer/stopper spring strips 65 is located away from the inner flange 151 of the protective cylinder 15, but may alternatively be disposed in abutment of the end thereof with the inner flange 151.

When each of the retainer/stopper spring strips 65 is located at an interval away from the inner flange 151 of the protective cylinder 15, it is advisable that the distance between each of the retainer/stopper spring strips 65 and the inner flange 151 be selected within a range which keeps the spring contacts 5 in electric contact with the sensor element 2 when the holder 6 moves relative to the protective cylinder 15.

Other arrangements are identical with those in the first embodiment, and explanation thereof in detail will be omitted here.

When the external force acts on the spring contacts 5 to pull the porcelain insulator 4 toward the base end of the gas sensor 1 along with the holder 6, it will cause the retainer/stopper spring strips 65 to be brought into abutment with the inner flange 151 of the protective cylinder 15 to stop the porcelain insulator 4 from moving out of the protective cylinder 15.

The protective cylinder 15 is joined to the housing 3. The sensor element 2 is also retained by the housing 3. Therefore, unless moved relative to the protective cylinder 15, the porcelain insulator 4 is not moved out of alignment with the sensor element 2. The spring contacts 5 are also held in place within the porcelain insulator 4, thus ensuring the stability of electrical contacts with the sensor element 2.

Specifically, the structure of the gas sensor 1 is designed to hold the spring contacts 5 in place within the porcelain insulator 4 free from the action of external force pulling the spring contacts 5 outside the porcelain insulator 4, thus ensuring the stability of electrical contacts with the terminals 25 of the sensor element 2.

When the air cover 11 is subjected to an external force and deformed, the space between the air cover 11 and the protective cylinder 15 serves to absorb such deformation, thereby avoiding the breakage of the sensor element 2.

Figure 6:
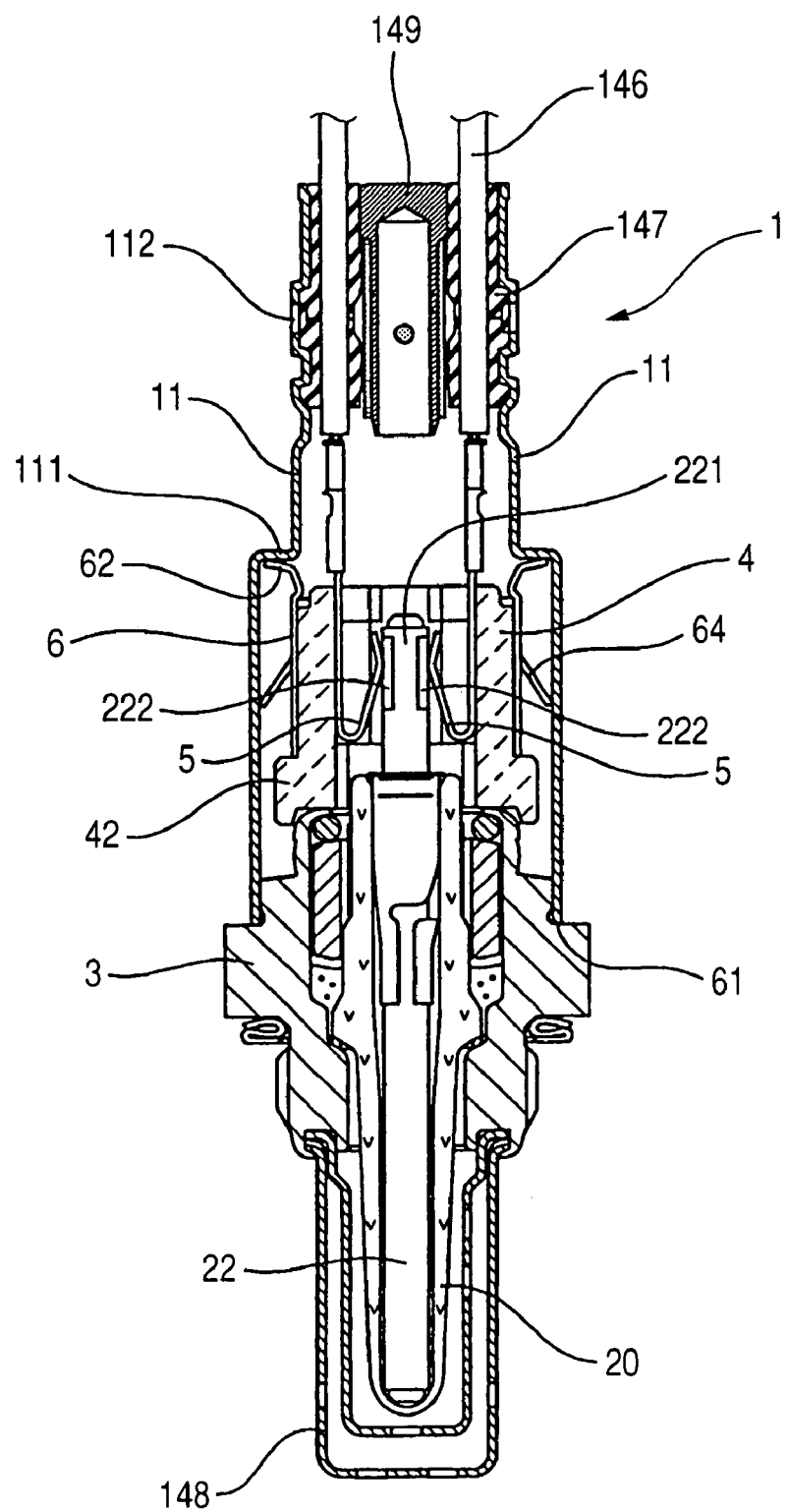
FIG. 6 is a longitudinal sectional view which shows a structure of a gas sensor according to the third embodiment of the invention.
Figure 7:
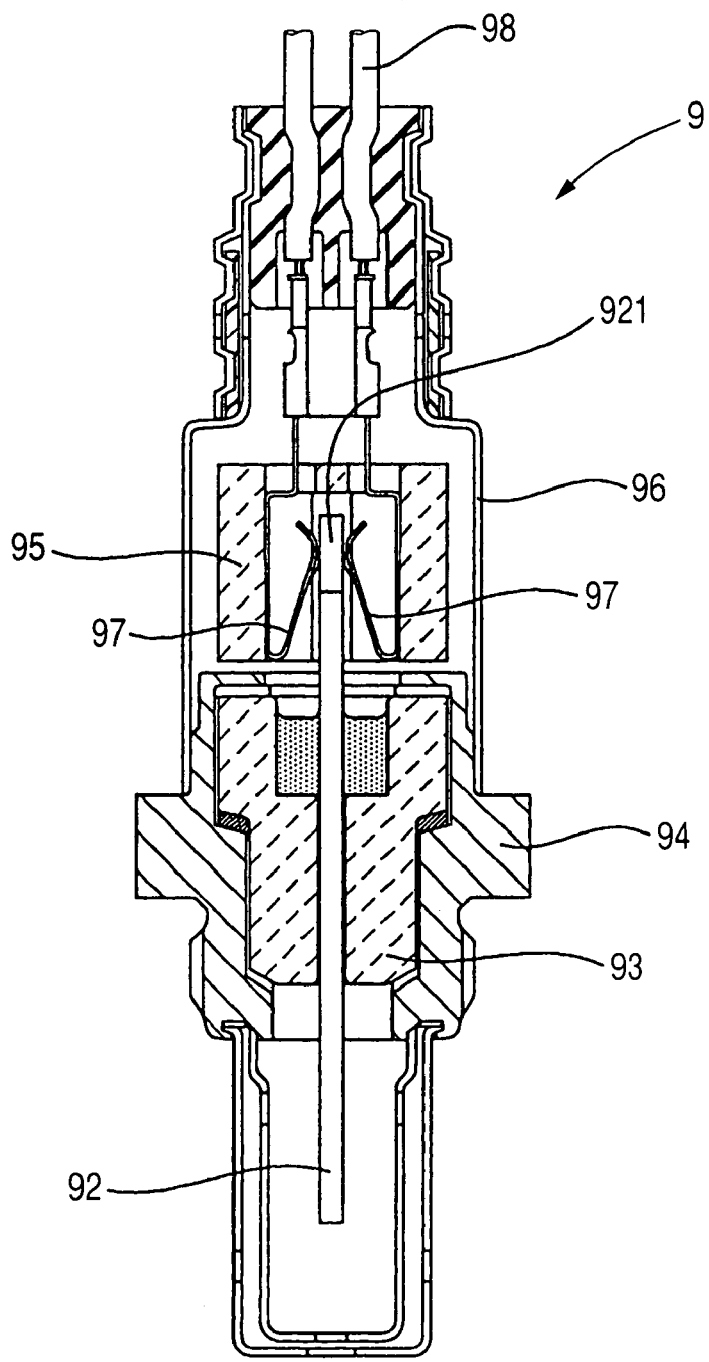
FIG. 7 is a longitudinal sectional view which shows a conventional gas sensor.

FIG. 6 illustrates the gas sensor 1 according to the third embodiment of the invention which is equipped with a cup-shaped sensor element 20.

The sensor element 20 of this type is well known and includes a hollow cylindrical solid electrolyte body with a bottom and a pair of electrodes (not shown) affixed to an outer and an inner surface of the solid electrolyte body.

The sensor element 20 is retained inside the housing 3. A heater 22 is disposed inside the sensor element 20 to heat it up to a desired activation temperature. The heater 22 is implemented by a cylindrical ceramic heater made of alumina and has a base end 221 extending outside the sensor element 20.

The porcelain insulator 4 is disposed on the base end of the housing 3 to cover the base end 221 of the heater 22.

The two spring contacts are fit between the inner wall of the porcelain insulator 4 and the base end 221 of the heater 22 to urge ends thereof radially into elastic abutment with terminals 222 affixed to the base end 221 of the heater 22. The terminals 222 lead to a heating element of the heater 22 to transmit electric power, as supplied through the leads 146, to the heating element.

Other arrangements are identical with those in the first embodiment, and explanation thereof in detail will be omitted here.

The structure of this embodiment, like the first embodiment, works to avoid the shifting of the porcelain insulator 4 from the air cover 11.

The air cover 11 is joined to the housing 3. The heater 22 is retained by the housing 3 through the sensor element 22. Therefore, unless moved relative to the air cover 11, the porcelain insulator 4 is not moved out of alignment with the heater 22, thereby ensuring the stability of electrical contact of the spring contacts 5 with the heater 22.

Specifically, the structure of the gas sensor 1 is designed to hold the spring contacts 5 in place within the porcelain insulator 4 free from the action of external force pulling the spring contacts 5 toward the base end of the gas sensor 1, thus ensuring the stability of electrical contact with the terminals 222 of the sensor element 22.

The structures of the second and third embodiments may be combined. For instance, the gas sensor 1, as illustrated in FIG. 5, may be equipped with the cup-shaped sensor element 20, as illustrated in FIG. 6, which is disposed inside the porcelain insulator 4 in electrical contact with the spring contacts 5.

While the present invention has been disclosed in terms of the preferred embodiments in order to facilitate better understanding thereof, it should be appreciated that the invention can be embodied in various ways without departing from the principle of the invention. Therefore, the invention should be understood to include all possible embodiments and modifications to the shown embodiments witch can be embodied without departing from the principle of the invention as set forth in the appended claims.

What is claimed is:

1. A gas sensor having a length with a top end and a base end opposite the top end, comprising:

a sensor element having a length with a top end and a base end opposite the top end, said sensor element being responsive to a gas to output a signal as a function of a concentration of the gas;

a housing having a top end and a base end opposite the top end, said housing retaining said sensor element therewithin;

a hollow porcelain insulator having a top end and a base end opposite the top end, said porcelain insulator being disposed on a side of the base end of said housing to cover the base end of said sensor element, said porcelain insulator having a protrusion formed on the top end thereof and a stopper formed therein;

a contact member disposed inside said porcelain insulator in electrical contact with a terminal of said sensor element, said contact member having a stopper which is placed in engagement with the stopper of said porcelain insulator for stopping said contact member from moving outside said porcelain insulator;

a holder having a top end and a base end opposite the top end, said holder grasping an outer surface of said porcelain insulator in engagement of the top end thereof with the protrusion of said porcelain insulator;

a cover disposed on the side of the base end of said housing in connection with the housing to cover said porcelain insulator, said cover having an inner stopper formed on an inner wall thereof; and a holder stopper formed on said holder which is designed to abut the inner stopper of said cover to stop said holder from moving to the base end of the gas sensor to hold said porcelain insulator from moving to the base end of the gas sensor through the engagement of the top end of said holder with the protrusion of said porcelain insulator.

2. A gas sensor as set forth in claim 1, wherein said holder stopper is designed to be elastically deformable when subjected to pressure oriented in a lengthwise direction of the gas sensor.

3. A gas sensor as set forth in claim 2, wherein said holder stopper has a bend which permits said holder stopper to be elastically deformed when subjected to the pressure.

4. A gas sensor as set forth in claim 1, wherein said holder grasps 50% or more of a circumference of the outer surface of said porcelain insulator.

5. A gas sensor having a length with a top end and a base end opposite the top end, comprising:

a sensor element having a length with a top end and a base end opposite the top end, said sensor element being responsive to a gas to output a signal as a function of a concentration of the gas;

a housing having a top end and a base end opposite the top end, said housing retaining said sensor element therewithin;

a hollow porcelain insulator having a top end and a base end opposite the top end, said porcelain insulator being disposed on a side of the base end of said housing to cover the base end of said sensor element, said porcelain insulator having a protrusion formed on the top end thereof and a stopper formed therein;

a contact member disposed inside said porcelain insulator in electrical contact with a terminal of said sensor element, said contact member having a stopper which is placed in engagement with the stopper of said porcelain insulator for stopping said contact member from moving outside said porcelain insulator;

a holder having a top end and a base end opposite the top end, said holder grasping an outer surface of said porcelain insulator in engagement of the top end thereof with the protrusion of said porcelain insulator;

a cover disposed on the side of the base end of said housing in connection with the housing to cover said porcelain insulator;

a protective cylinder having a top end and a base end opposite the top end, said protective cylinder being joined to said housing and located outside said porcelain insulator within said cover;

a holder stopper formed on said holder, said holder stopper being urged into abutment with an inner surface of said protective cylinder; and a protrusion formed on the base end of said protective cylinder, said protrusion extending inwardly of said protective cylinder to server as a stopper which is designed to abut said holder stopper to stop said holder from moving to the base end of the gas sensor to hold said porcelain insulator from moving to the base end of the gas sensor through the engagement of the top end of said holder with the protrusion of said porcelain insulator.

6. A gas sensor as set forth in claim 5, wherein said holder grasps 50% or more of a circumference of the outer surface of said porcelain insulator.

7. A gas sensor having a length with a top end and a base end opposite the top end, comprising:

a hollow cylindrical sensor element with a bottom which has a length with a top end and a base end opposite the top end, said sensor element being responsive to a gas to output a signal as a function of a concentration of the gas;

a housing having a top end and a base end opposite the top end, said housing retaining said sensor element therewithin;

a heater having a top end and a base end opposite the top end, said heater being disposed inside said sensor element with the base end thereof protruding outside said sensor element to heat said sensor element;

a hollow porcelain insulator having a top end and a base end opposite the top end, said porcelain insulator being disposed on a side of the base end of said housing to cover the base end of said heater, said porcelain insulator having a protrusion formed on the top end thereof and a stopper formed therein;

a contact member disposed inside said porcelain insulator in electrical contact with a terminal of said heater, said contact member having a stopper which is placed in engagement with the stopper of said porcelain insulator for stopping said contact member from moving outside said porcelain insulator;

a holder having a top end and a base end opposite the top end, said holder grasping an outer surface of said porcelain insulator in engagement of the top end thereof with the protrusion of said porcelain insulator;

a cover disposed on the side of the base end of said housing in connection with the housing to cover said porcelain insulator, said cover having an inner stopper formed on an inner wall thereof; and a holder stopper formed on said holder which is designed to abut the inner stopper of said cover to stop said holder from moving to the base end of the gas sensor to hold said porcelain insulator from moving to the base end of the gas sensor through the engagement of the top end of said holder with the protrusion of said porcelain insulator.

8. A gas sensor as set forth in claim 7, wherein said holder stopper is designed to be elastically deformable when subjected to pressure oriented in a lengthwise direction of the gas sensor.

9. A gas sensor as set forth in claim 8, wherein said holder stopper has a bend which permits said holder stopper to be elastically deformed when subjected to the pressure.

10. A gas sensor as set forth in claim 7, wherein said holder grasps 50% or more of a circumference of the outer surface of said porcelain insulator.

11. A gas sensor having a length with a top end and a base end opposite the top end, comprising:

a hollow cylindrical sensor element with a bottom which has a length with a top end and a base end opposite the top end, said sensor element being responsive to a gas to output a signal as a function of a concentration of the gas;

a housing having a top end and a base end opposite the top end, said housing retaining said sensor element therewithin;

a heater having a top end and a base end opposite the top end, said heater being disposed inside said sensor element with the base end thereof protruding outside said sensor element to heat said sensor element;

a hollow porcelain insulator having a top end and a base end opposite the top end, said porcelain insulator being disposed on a side of the base end of said housing to cover the base end of said heater, said porcelain insulator having a protrusion formed on the top end thereof and a stopper formed therein;

a contact member disposed inside said porcelain insulator in electrical contact with a terminal of said heater, said contact member having a stopper which is placed in engagement with the stopper of said porcelain insulator for stopping said contact member from moving outside said porcelain insulator;

a holder having a top end and a base end opposite the top end, said holder grasping an outer surface of said porcelain insulator in engagement of the top end thereof with the protrusion of said porcelain insulator;

a cover disposed on the side of the base end of said housing in connection with the housing to cover said porcelain insulator;

a protective cylinder having a top end and a base end opposite the top end, said protective cylinder being joined to said housing and located outside said porcelain insulator within said cover;

a holder stopper formed on said holder, said holder stopper being urged into abutment with an inner surface of said protective cylinder; and a protrusion formed on the base end of said protective cylinder, said protrusion extending inwardly of said protective cylinder to server as a stopper which is designed to abut said holder stopper to stop said holder from moving to the base end of the gas sensor to hold said porcelain insulator from moving to the base end of the gas sensor through the engagement of the top end of said holder with the protrusion of said porcelain insulator.

12. A gas sensor as set forth in claim 11, wherein said holder grasps 50% or more of a circumference of the outer surface of said porcelain insulator.

* * * * *